US009121815B2

(12) United States Patent
Lee et al.

(10) Patent No.: US 9,121,815 B2
(45) Date of Patent: Sep. 1, 2015

(54) METHOD FOR MEASURING FIBER CONTENT OF POLYETHYLENETEREPHTHALATE AND POLYTRIMETHYLENETEREPHTHALATE FIBERS

(71) Applicant: Hyundai Motor Company, Seoul (KR)

(72) Inventors: Keum-hyang Lee, Seoul (KR); Min-Chul Shin, Seoul (KR); Eun-Ho Shin, Seoul (KR)

(73) Assignee: Hyundai Motor Company, Seoul (KR)

( * ) Notice: Subject to any disclaimer, the term of this patent is extended or adjusted under 35 U.S.C. 154(b) by 189 days.

(21) Appl. No.: 13/873,582

(22) Filed: Apr. 30, 2013

(65) Prior Publication Data
US 2014/0185032 A1 Jul. 3, 2014

(30) Foreign Application Priority Data

Dec. 28, 2012 (KR) ........................ 10-2012-0155925

(51) Int. Cl.
*G01J 5/02* (2006.01)
*G01N 21/23* (2006.01)
(52) U.S. Cl.
CPC .. *G01N 21/23* (2013.01); *G01J 5/02* (2013.01)
(58) Field of Classification Search
CPC .......................................................... G01J 5/10

USPC ....................................................... 250/338.1
See application file for complete search history.

(56) References Cited

FOREIGN PATENT DOCUMENTS

| CN | 101504358 A | * | 8/2009 |
|----|-------------|---|--------|
| JP | 2011047759 A | | 3/2011 |
| JP | 2011203138 A | | 10/2011 |
| KR | 10-1993-0005525 B1 | | 6/1993 |
| KR | 10-2007-0034647 A | | 3/2007 |

* cited by examiner

*Primary Examiner* — Christine Sung
(74) *Attorney, Agent, or Firm* — Mintz Levin Cohn Ferris Glovsky and Popeo, P.C.; Peter F. Corless (57) ABSTRACT

Disclosed is a method for measuring a fiber content of polyethyleneterephthalate (PET) and polytrimethyleneterephthalate (PTT) fibers, particularly wherein the method includes: a qualitative analysis step of identifying a presence of polyethyleneterephthalate (PET) and polytrimethyleneterephthalate (PTT) fibers in a mixed-spun fiber product; and a quantitative analysis step of measuring the fiber content by a microscopic count through difference in color between PET and PTT fibers by birefringence in a cross polarization state of a polarized light microscope (PLM). Through the present invention, it is possible to simply and accurately calculate the fiber content of PET and PTT fibers in a mixed-spun fiber material in which various kinds of fibers are mixed.

4 Claims, 7 Drawing Sheets

FIG. 1

YARN

NONWOVEN FABRIC

PRIOR ART

METHOD FOR MEASURING FIBER CONTENT OF POLYETHYLENETEREPHTHALATE AND POLYTRIMETHYLENETEREPHTHALATE FIBERS

CROSS-REFERENCE TO RELATED APPLICATIONS

The present application claims priority to Korean Patent Application No. 10-2012-0155925, filed on Dec. 28, 2012, the entire contents of which is incorporated herein for all purposes by this reference

BACKGROUND OF THE INVENTION

1. Field of the Invention

The present invention relates to a method for measuring a fiber content in a mixed-spun fiber, particularly a method for measuring fiber content of polyethyleneterephthalate (PET) and polytrimethyleneterephthalate (PTT) fibers in a mixed-spun fiber. More particularly, the present invention relates to a method for measuring the fiber content of PET and PTT fibers in a mixed-spun fiber material in which various types of fibers are mixed by using a polarized light microscope.

2. Description of the Related Art

Figure 1:
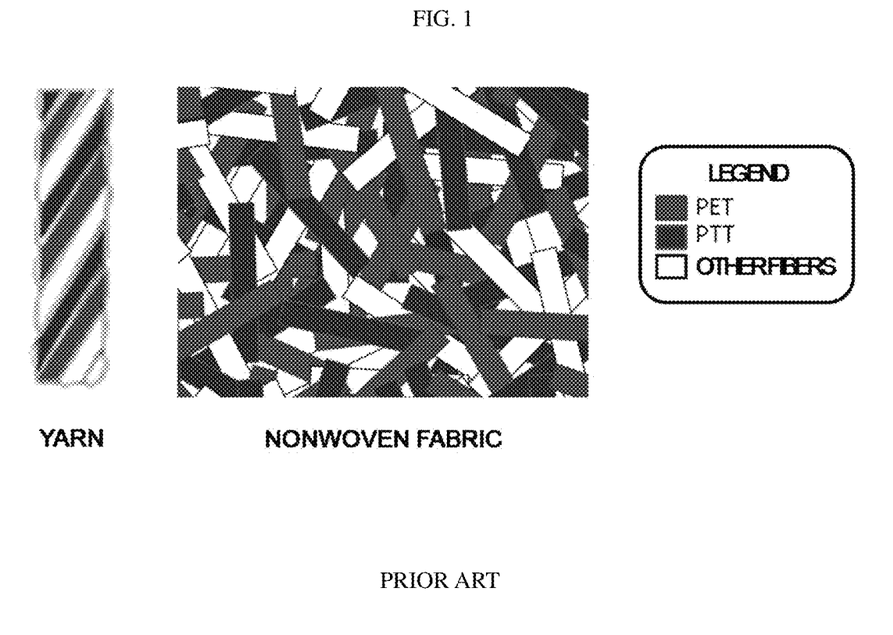
FIG. 1 is a conceptual view illustrating the forms of PET and PTT present in a conventional yarn and a non-woven fabric.

FIG. 1 is a view illustrating the structure of a conventional fiber product in which polyethyleneterephthalate (PET) fiber, polytrimethyleneterephthalate (PTT) fiber, and other fiber components are mixed-spun.

As illustrated, a product is manufactured by mixing the PET and PTT fibers without using the PET fiber alone because this makes it possible to improve elastic force without using spandex fiber. This is beneficial because the PTT fiber has excellent elastic recovery durability whereas the elastic recovery force of the spandex fiber is reduced by repeated elongation thereof several times.

The PET fiber and PTT fiber may be represented by the following Formula 1.

[Formula 1]

Formula of PET fiber

Formula of PTT fiber

When the content of the PTT fiber is increased in a fiber product, touch and elasticity are improved. However, the PTT fiber is expensive, and thus a desired physical property may be implemented while reducing the cost by mixing relatively inexpensive PET fiber therewith.

TABLE 1

| Classification | PTT | PET |
|---|---|---|
| Touch | Soft touch | Stiff touch compared to PTT |
| Elasticity | Excellent | Insufficient |
| Dyeability | Excellent | Excellent |
| Dyeing temperature | 110° C. | 130° C. |
| Glass transition temperature (Tg) | 45 to 65° C. | 69 to 115° C. |
| Melting temperature (Tm) | 228° C. | 265° C. |
| Heat treatment temperature | 140° C. | 180° C. |
| Price | High | Reasonable |

Table 1 is a table that compares general physical properties of PTT and PET fibers, and required physical properties are satisfied by controlling the content of each component so as to provide suitable characteristics and physical properties required for various kinds of fiber products.

In the related art, when the PTT fiber is mixed-spun with other fibers which are different in solubility and form, the content thereof may be measured. However, when the PTT fiber is mixed-spun with PET fiber, which is the same the PTT fiber in solubility and form, there is a problem in that there is no method of measuring the fiber content thereof.

SUMMARY OF THE INVENTION

The present invention provides a method for measuring a fiber content of polyethyleneterephthalate (PET) and polytrimethyleneterephthalate (PTT) fibers in a mixed-spun fiber. In particular, the present invention provides a method for measuring fiber content by observing the PET and PTT fibers in a cross polarization state of a polarized light microscope, which distinguishes the PET fibers and the PTT fibers through differences in color by birefringence of the fibers.

According to one aspect, the present invention provides a method for measuring a fiber content of polyethyleneterephthalate (PET) and polytrimethyleneterephthalate (PTT) fibers, including: a qualitative analysis step of identifying a presence of polyethyleneterephthalate (PET) and polytrimethyleneterephthalate (PTT) fibers in a mixed-spun fiber product; and a quantitative analysis step of measuring the fiber content by a microscopic count through differences in color between PET and PTT fibers by birefringence in a cross polarization state of a polarized light microscope (PLM).

According to various embodiments, it is preferred that the qualitative analysis step identifies the presence of a fiber by using Fourier Transform Infrared Spectroscopy (FT-IR) and Differential Scanning Calorimetry (DSC).

According to various embodiments of the present invention, it is preferred that the quantitative analysis step measures the fiber content by the following Equations 1 and 2 when a cross-section of the fiber is circular.

$$\text{Fiber content}_{PTT}(\%) = \frac{Number_{PTT} \times Diameter_{PTT}^2 \times \text{Specific weight}_{PTT}}{Number_{PTT} \times Diameter_{PTT}^2 \times \text{Specific weight}_{PTT} + Number_{PET} Diameter_{PET}^2 \times \text{Specific weight}_{PET}} \times 100$$ [Equation 1]

$$\text{Fiber content}_{PET}(\%) = 100 - \text{Fiber content}_{PTT}$$ [Equation 2]

According to various embodiments of the present invention, it is preferred that the quantitative analysis step measures the fiber content by the following Equations 3 and 4 when a cross-section of the fiber is not circular.

$$\text{Fiber content}_{PTT}(\%) = \quad\quad\quad\quad\quad\quad\quad\quad\quad\quad\quad [\text{Equation 3}]$$

$$\frac{Number_{PTT} \times \text{Cross-sectional } area_{PTT} \times \text{Specific } weight_{PTT}}{\begin{array}{c}Number_{PTT} \times \text{Cross-sectional } area_{PTT} \times \\ \text{Specific } weight_{PTT} + \\ Number_{PET} \times \text{Cross-sectional } area_{PTT} \times \\ \text{Specific } weight_{PET}\end{array}} \times 100$$

$$\text{Fiber content}_{PET}(\%) = 100 - \text{Fiber content}_{PTT} \quad [\text{Equation 4}]$$

According to the present invention, there is an advantage in that in a mixed-spun product of PET and PTT fibers, which is increasingly being utilized in forming fiber products and fiber materials for automobiles, the fiber content of the PET and PTT fibers may be measured with high accuracy.

In addition, the measurement method according to the present invention is advantageous in that the method is simple and useful and, thus, may be utilized in identification of whether a fiber product, particularly, a fiber material for an automobile, complies with the required standards, addresses potential quality problem, prevents defects, achieves benchmarks, and the like.

Other features and aspects of the present invention will be apparent from the following detailed description, drawings and claims.

It should be understood that the appended drawings are not necessarily to scale, presenting a somewhat simplified representation of various preferred features illustrative of the basic principles of the invention. The specific design features of the invention as disclosed herein, including, for example, specific dimensions, orientations, locations and shapes, will be determined in part by the particular intended application and use environment. The specific solar cell type of the invention as disclosed herein will be determined in part by the particular intended application and use environment.

In the figures, reference numerals refer to the same or equivalent parts of the disclosure throughout the several figures of the drawings.

DETAILED DESCRIPTION OF THE EMBODIMENTS

Terms or words used in the present specification and claims should not be interpreted as being limited to typical or dictionary meanings, but should be interpreted as having meanings and concepts, which comply with the technical spirit of the present invention, based on the principle that an inventor can appropriately define the concept of the term to describe his/her own invention in the best manner. Therefore, configurations illustrated in the embodiments and the drawings described in the present specification are only the most preferred embodiment of the present invention and do not represent all of the technical spirit of the present invention, and thus it is to be understood that various modified examples, which may replace the configurations, are possible when filing the present application.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about".

Hereinafter, the present invention will be described in detail with reference to the accompanying drawings.

The present invention is an application of a microscopic count method used for an analysis of a fiber content in a fiber product. Further, according to the present invention, for the qualitative analysis of the PET and PTT fibers, Fourier Transform Infrared Spectroscopy (FT-IR) and Differential Scanning Calorimetry (DSC) are first used.

In general, in the quantitative analysis in the related art, when fibers are different from each other in solubility in a drug in a state at which several kinds of fibers are mixed-spun, the weight percentage is obtained by dissolving each fiber in the drug, and then measuring the weight difference. However, in a case where different kinds of fibers are dissolved in the same drug, when it is observed that the shapes of the fibers are different on a microscope slide glass by using a microscope, the diameter thereof is measured in a circular shape of the fibers, and the cross-sectional area thereof is measured in a non-circular shape of the fiber. The fiber content is then analyzed by counting until the sum of the different kinds of fibers reaches 1,000 or more.

However, in such a method, since the PET and PTT fibers are dissolved in the same drug, the forms observed with the naked eyes during the observation through a microscope are the same as each other. Thus, there is a problem in that it is impossible to analyze the content thereof through the microscopic counting method in the related art.

According to the present invention, PET and PTT fibers are observed in the cross polarization (crossed nicol) state of a polarized light microscope. In this state, fibers may be counted with the naked eyes through the difference in birefringence color by molecules of each fiber and crystal formation regardless of whether the fiber is dyed or not. In the case of a product in which other fibers are mixed-spun in addition to the PET and PTT fibers, the fiber content is calculated with the weight ratio of the other fibers by dissolving the other fibers using a drug.

Specifically, the method for measuring a fiber content according to an embodiment of the present invention includes a qualitative analysis step of indentifying whether PET and PTT fibers are present in a mixed-spun fiber; and a quantitative analysis step of measuring the fiber content by a microscopic count through differences in color between PET and PTT fibers by birefringence in a cross polarization state of a polarized light microscope (PLM). This method will be described in further detail below.

1. Qualitative Analysis Step

Figure 2:
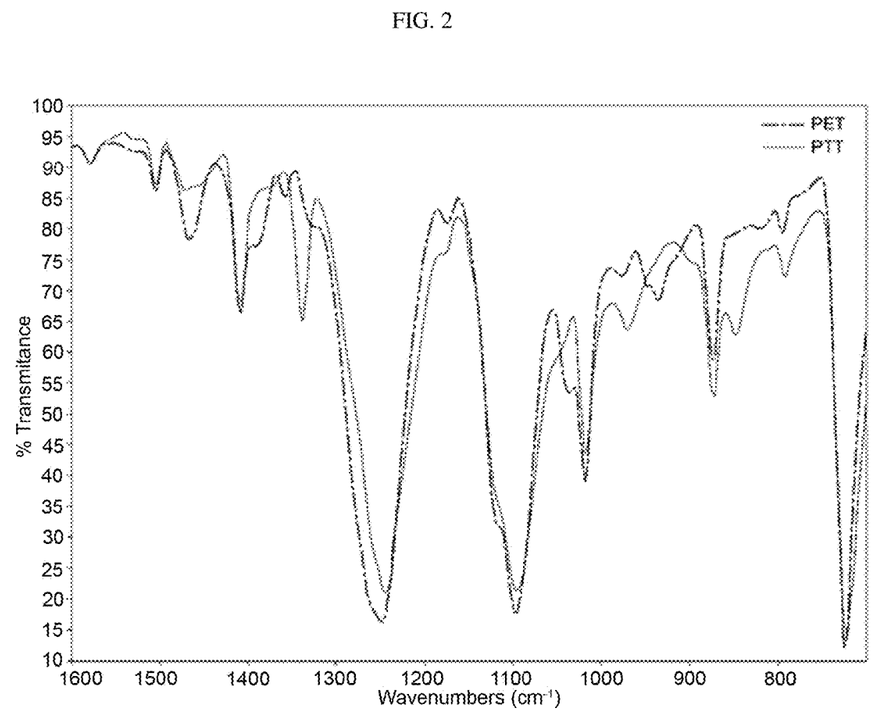
FIG. 2 is a spectrum of characteristic peaks of 100% PET fiber and 100% PTT fiber which are identified in an FT-IR ATR spectrum according to an embodiment of the present invention.
Figure 3:
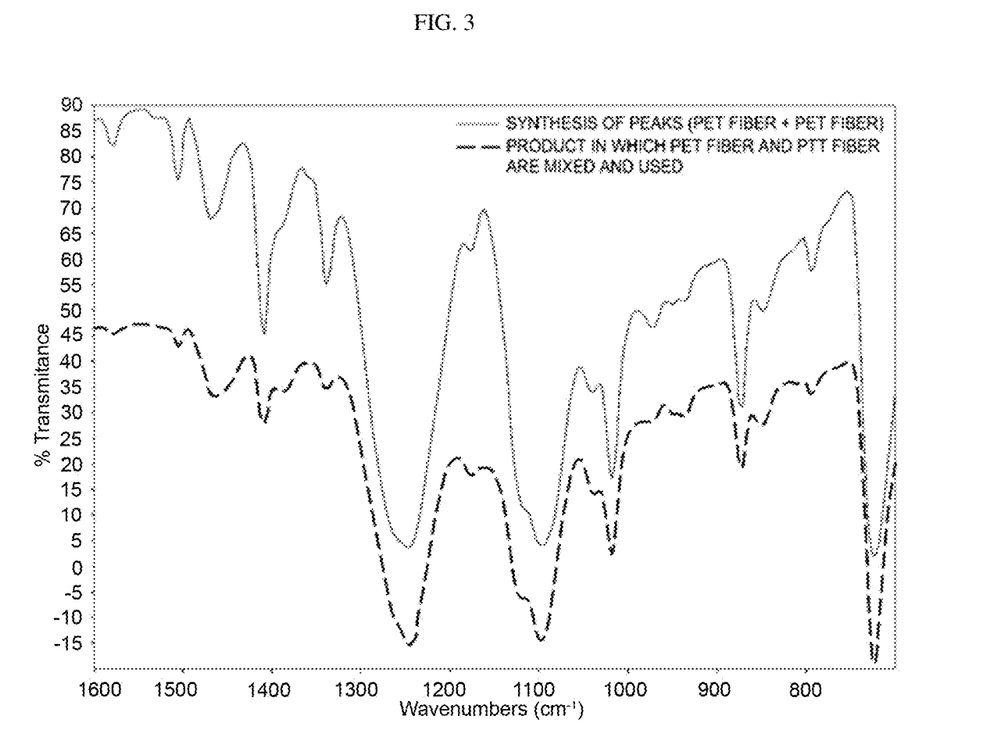
FIG. 3 is a spectrum obtained by synthesizing the peaks of the PET fiber and the peaks of the PTT fiber in FIG. 2 and a spectrum of characteristic peaks of a fiber product in which the PET and PTT fibers are mixed and used according to an embodiment of the present invention.
Figure 4:
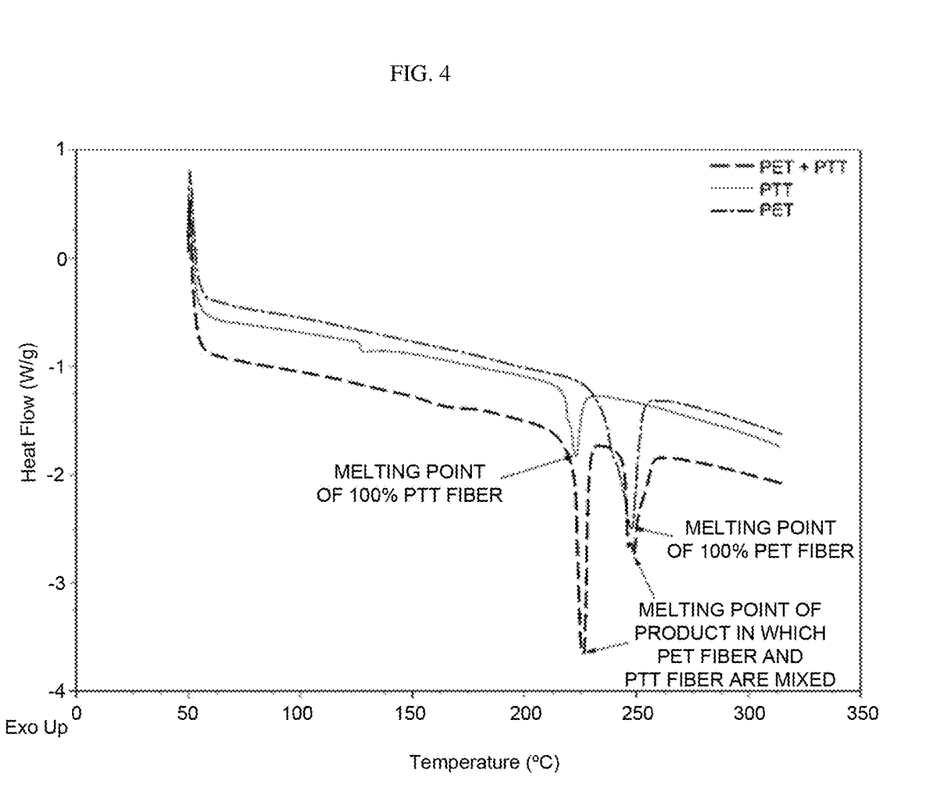
FIG. 4 is a result of the melting points of PET and PTT fibers identified in the DSC spectrum according to an embodiment of the present invention.

The qualitative analysis step is a step that identifies whether PET and PTT fibers are present in a mixed-spun fiber product. In particular, the presence of the PET and PTT fibers may be identified by comparing the spectra and melting temperatures of the PET and PTT fibers using Fourier Transform Infrared Spectroscopy (FT-IR) and Differential Scanning Calorimetry (DSC) (see FIGS. 2 to 4).

2. Quantitative Analysis Step

Figure 5:
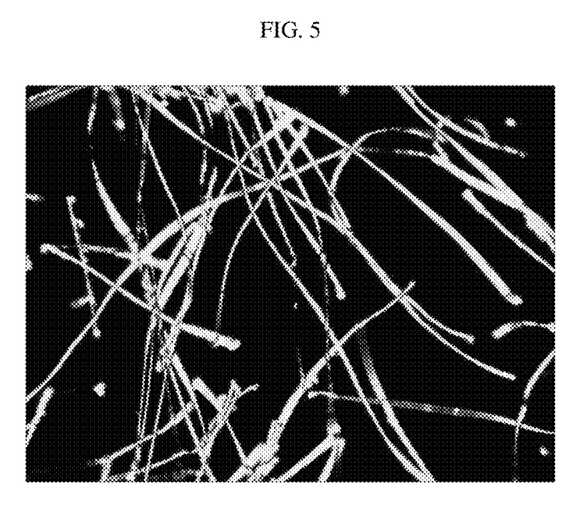
FIG. 5 is a birefringence color of the 100% PET fiber observed in a cross polarization state of a polarized light microscope according to an embodiment of the present invention.
Figure 6:
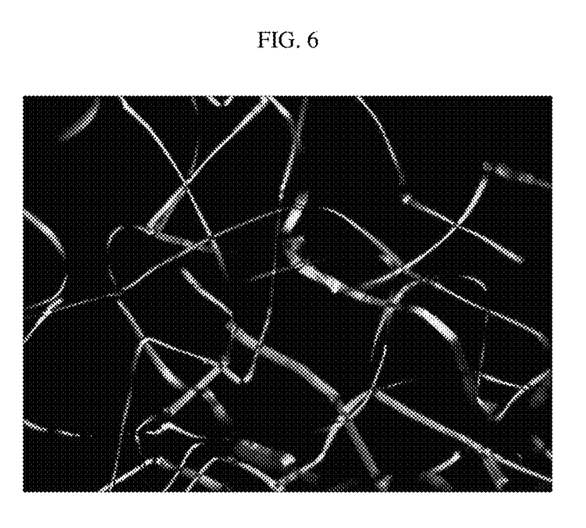
FIG. 6 is a birefringence color of the 100% PTT fiber observed in a cross polarization state of a polarized light microscope according to an embodiment of the present invention.
Figure 7:
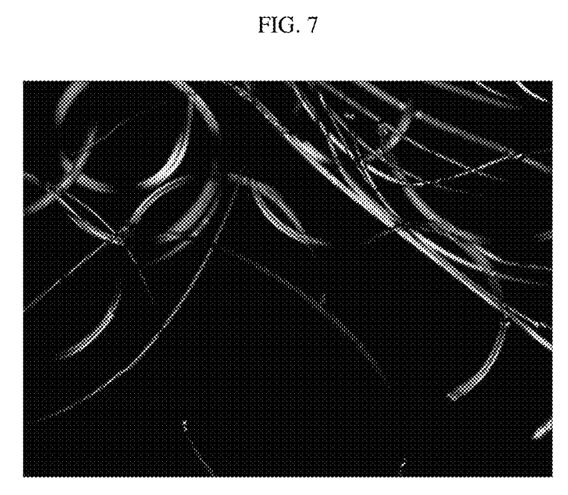
FIG. 7 is a birefringence color when the PET and PTT fibers observed in a cross polarization state of a polarized light microscope are mixed and used according to an embodiment of the present invention.

The quantitative analysis step is a step that measures the fiber content by a microscopic count through difference in birefringence color between PET and PTT fibers placed on a slide glass for observation by utilizing a cross polarization observation mode of a polarized light microscope (PLM) (see FIGS. 5 to 7).

In particular, the fiber content may be measured by observing the birefringence colors of PET and PTT fibers in a cross polarization observation mode of a polarized light microscope, measuring the diameter or cross-sectional area of each fiber, multiplying the obtained value with a specific weight to obtain an average weight of each kind of fiber, counting the number of fibers contained in the material and product, and multiplying the average weight with the count value of each fiber.

According to an embodiment of the present invention, when the cross-sections of the fibers are circular, it is preferred that the fiber content is measured through the following Equations 1 and 2 by measuring the diameter, the number and the like of each fiber.

$$\text{Fiber } content_{PTT}(\%) = \frac{Number_{PTT} \times Diameter_{PTT}^2 \times \text{Specific } weight_{PTT}}{\substack{Number_{PTT} \times Diameter_{PTT}^2 \times \text{Specific } weight_{PTT} + \\ Number_{PET} Diameter_{PET}^2 \times \text{Specific } weight_{PET}}} \times 100 \quad \text{[Equation 1]}$$

$$\text{Fiber } content_{PET}(\%) = 100 - \text{Fiber } content_{PTT} \quad \text{[Equation 2]}$$

(Fiber content$_{PTT}$, Number$_{PTT}$, Diameter$_{PTT}$, and Specific weight$_{PTT}$ mean the fiber content, number, diameter, and specific weight of PTT fiber, respectively; and Fiber content$_{PET}$, Number$_{PET}$, Diameter$_{PET}$, and Specific weight$_{PET}$ mean the fiber content, number, diameter, and specific weight of PET fiber, respectively)

Furthermore, when the cross-sections of the fibers are not circular, it is preferred that the fiber content is measured through the following Equations 3 and 4 by measuring the cross-sectional area, the number and the like of each fiber.

$$\text{Fiber } content_{PTT}(\%) = \frac{\substack{Number_{PTT} \times \text{Cross-sectional } area_{PTT} \times \\ \text{Specific } weight_{PTT}}}{\substack{Number_{PTT} \times \text{Cross-sectional } area_{PTT} \times \\ \text{Specific } weight_{PTT} + \\ Number_{PET} \times \text{Cross-sectional } area_{PET} \times \\ \text{Specific } weight_{PET}}} \times 100 \quad \text{[Equation 3]}$$

$$\text{Fiber } content_{PET}(\%) = 100 - \text{Fiber } content_{PTT} \quad \text{[Equation 4]}$$

(Fiber content$_{PTT}$, Number$_{PTT}$, Cross-sectional area$_{PTT}$, and Specific weight$_{PTT}$ mean the fiber content, number, cross-sectional area, and specific weight of PTT fiber, respectively; and Fiber content$_{PET}$, Number$_{PET}$, Cross-sectional area$_{PET}$, and Specific weight$_{PET}$ mean the fiber content, number, cross-sectional area, and specific weight of PET fiber, respectively)

Through the Equations 1 to 4, the fiber content of PET and PTT fibers is calculated. As such, the present invention may be widely used during the physical property estimation of a material, the development of a new material, benchmarking, in response to a quality problem and the like.

Hereinafter, the present invention will be described in more detail through Examples. These Examples are only for illustrating the present invention, and it will be obvious to those skilled in the art that the scope of the present invention is not interpreted to be limited by these Examples.

EXAMPLE 1

PTT fiber is a component which influences mechanical properties and chemical resistance. A reference specimen (the cross-section of the fiber was circular) containing the PTT fiber in an amount of 50.1% by weight based on the total weight was prepared, and the analysis results according to the above Equations are shown in the following Table 2.

TABLE 2

| Prepared specimen | | | Analysis result | | |
|---|---|---|---|---|---|
| Component | Fiber content (%) | Average diameter (μm) | Specific weight | Number | Calculation result Fiber content (%) |
| PTT fiber | 50.1 | 11.06 | 1.27 | 645 | 47.5 |
| PET fiber | 49.9 | 15.08 | 1.37 | 355 | 52.5 |

As illustrated in Table 2, the fiber content measured by using the Equations and the actual fiber content were significantly similar to each other. Thus, the reliability of the measurement method according to the present invention was confirmed.

Further, for evaluating reproducibility through repeated measurement, the measurement test was further performed three times, and the results thereof are shown in the following Table 3.

TABLE 3

| Prepared specimen containing PTT fiber in an amount of 50.1% by weight | | Analysis result | |
|---|---|---|---|
| Number of measurements | Calculation result Fiber content of PTT fiber (% by weight) | Standard deviation | Average fiber content (% by weight) |
| #1 | 47.5 | 1.91 | 45.7 |
| #2 | 43.7 | | |
| #3 | 46.0 | | |

The reproducibility evaluation results of Table 3 are as follows when the test of the average using the t-distribution was performed.

Null hypothesis (H0): the fiber content of PTT fiber is 50.1% by weight.

Alternative hypothesis (H1): the fiber content of PTT fiber is not 50.1% by weight.

The statistical analysis results are as follows.

At the confidence level of 95%, the measurement result statistically ranged from 40.9787% by weight to 50.4879% by weight, and the p value was 0.058, which is larger than a significance level of 0.05. Thus, the null hypothesis was adopted. In other words, as the measurement result, the fiber content of PTT fiber may be said to be the same as 50.1% by weight.

At the confidence level of 99%, the measurement result statistically ranged from 34.7660% by weight to 56.7007% by weight, and the p value was 0.058, which is larger than a significance level of 0.01. Thus, the null hypothesis was adopted. In other words, as the measurement result, the fiber content of PTT fiber may be said to be the same as 50.1% by weight.

That is, through the test results, it was confirmed that the method for measuring a fiber content according to the present invention was very useful and simple, and the calculated fiber content of PTT and PET fibers was reliable with respect to the actual fiber content at the level of 95% or more.

As described above, the present invention has been described in relation to specific embodiments of the present invention, but this is only illustration and the present invention is not limited thereto. Embodiments described may be changed or modified by those skilled in the art to which the present invention pertains without departing from the scope of the present invention, and various alterations and modifications are possible within the technical spirit of the present invention and the equivalent scope of the claims which will be described below.

What is claimed is:

1. A method for measuring a fiber content of polyethyleneterephthalate (PET) and polytrimethyleneterephthalate (PTT) fibers, the method comprising:
    a qualitative analysis step of identifying a presence of polyethyleneterephthalate (PET) and polytrimethyleneterephthalate (PTT) fibers in a mixed-spun fiber product; and
    a quantitative analysis step of measuring the fiber content by a microscopic count through difference in color between PET and PTT fibers by birefringence in a cross polarization state of a polarized light microscope (PLM),
    wherein the quantitative analysis step measures the fiber content by the following Equations 1 and 2 when a cross-section of the fiber is circular $$\text{Fiber content}_{PTT}(\%) = \frac{\text{Number}_{PTT} \times \text{Diamter}_{PTT}^2 \times \text{Specific weight}_{PTT}}{\text{Number}_{PTT} \times \text{Diamter}_{PTT}^2 \times \text{Specific weight}_{PTT} + \text{Number}_{PET} \text{Diamter}_{PET}^2 \times \text{Specific weight}_{PET}} \times 100 \quad \text{[Equation 1]}$$

$$\text{Fiber content}_{PET}(\%) = 100 - \text{Fiber content}_{PTT}. \quad \text{[Equation 2]}$$

2. The method of claim 1, wherein the qualitative analysis step identifies the presence of a fiber by using Fourier Transform Infrared Spectroscopy (FT-IR) and Differential Scanning calorimetry (DSC).

3. A method for measuring a fiber content of polyethyleneterephthalate (PET) and polytrimethyleneterephthalate (PTT) fibers, the method comprising:
    a qualitative analysis step of identifying a presence of polyethyleneterephthalate (PET) and polytrimethyleneterephthalate (PTT) fibers in a mixed-spun fiber product; and
    a quantitative analysis step of measuring the fiber content by a microscopic count through difference in color between PET and PTT fibers by birefringence in a cross polarization state of a polarized light microscope (PLM),
    wherein the quantitative analysis step measures the fiber content by the following Equations 3 and 4 when a cross-section of the fiber is not circular $$\text{Fiber content}_{PTT}(\%) = \frac{\text{Number}_{PTT} \times \text{Cross-sectional area}_{PTT} \times \text{Specific weight}_{PTT}}{\text{Number}_{PTT} \times \text{Cross-sectional area}_{PTT} \times \text{Specific weight}_{PTT} + \text{Number}_{PET} \times \text{Cross-sectional area}_{PET} \times \text{Specific weight}_{PET}} \times 100 \quad \text{[Equation 3]}$$

$$\text{Fiber content}_{PET}(\%) = 100 - \text{Fiber content}_{PTT}. \quad \text{[Equation 4]}$$

4. The method of claim 3, wherein the qualitative analysis step identifies the presence of a fiber by using Fourier Transform Infrared Spectroscopy (FT-IR) and Differential Scanning calorimetry (DSC).

* * * * *